US008535310B2

(12) United States Patent  
Hardin, Jr. et al.

(10) Patent No.: US 8,535,310 B2  
(45) Date of Patent: Sep. 17, 2013

(54) SPHINCTEROTOME

(75) Inventors: David M. Hardin, Jr., Winston-Salem, NC (US); John A. Karpiel, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 11/835,837

(22) Filed: Aug. 8, 2007

(65) Prior Publication Data

US 2009/0043259 A1 Feb. 12, 2009

(51) Int. Cl.
*A61B 18/18* (2006.01)
*A61B 17/22* (2006.01)

(52) U.S. Cl.
USPC ............................ 606/47; 606/159

(58) Field of Classification Search
USPC ............. 606/113, 167, 46, 45, 159, 41, 86, 606/157, 47–49; 604/164.13, 164.05, 523, 604/528; 600/114, 564, 585
See application file for complete search history.

(56) References Cited

U.S. PATENT DOCUMENTS

| | | | | |
|---|---|---|---|---|
| 5,035,696 A | * | 7/1991 | Rydell | 606/47 |
| 5,163,938 A | * | 11/1992 | Kambara et al. | 606/47 |
| 5,788,681 A | * | 8/1998 | Weaver et al. | 604/523 |
| 5,810,807 A | * | 9/1998 | Ganz et al. | 606/47 |
| 5,868,698 A | | 2/1999 | Rowland | |
| 6,471,702 B1 | * | 10/2002 | Goto | 606/47 |
| 2003/0208219 A1 | | 11/2003 | Aznoian | |
| 2004/0039371 A1 | * | 2/2004 | Tockman et al. | 604/528 |
| 2004/0064128 A1 | * | 4/2004 | Raijman et al. | 604/523 |
| 2005/0192607 A1 | * | 9/2005 | Hutchins et al. | 606/167 |
| 2006/0030864 A1 | | 2/2006 | Kennedy, II et al. | |
| 2007/0118112 A1 | * | 5/2007 | Kennedy, II | 606/45 |
| 2008/0214890 A1 | * | 9/2008 | Motai et al. | 600/107 |
| 2009/0005778 A1 | * | 1/2009 | Ducharme | 606/46 |
| 2009/0043259 A1 | | 2/2009 | Hardin, Jr. et al. | |

FOREIGN PATENT DOCUMENTS

| WO | WO 01/89603 A1 | 11/2001 |
|---|---|---|
| WO | WO 2006/015323 A2 | 2/2006 |

* cited by examiner

*Primary Examiner* — Tuan V Nguyen
*Assistant Examiner* — Tin Nguyen
(74) *Attorney, Agent, or Firm* — Brinks Hofer Gilson & Lione

(57) ABSTRACT

A medical sphincterotome and a method of its use are described. The sphincterotome has structural elements that are capable of directing a wire guide through a selected body passageway. One structural element includes a distal port and deflection member that can deflect the wire guide into the desired passageway. Another structural element includes an offset nose-shaped end that can bend towards a passageway desired to be blocked. The wire guide is prevented from entering the blocked passageway, thereby enabling the wire guide to cannulate the desired passageway. The sphincterotome also includes a cutting wire to access a patient's sphincter and perform various other medical procedures.

16 Claims, 5 Drawing Sheets

SPHINCTEROTOME

TECHNICAL FIELD

The invention generally relates to a medical device which selectively directs a wire guide into a branched body passageway.

BACKGROUND

Navigating a medical device through a body passage can be difficult when attempting to maneuver within a selected branching pathway, such as a bifurcated duct or vessel. For example, most wire guides lack the ability to maneuver in a particular direction, especially when the direction is against the natural pathway that the wire guide prefers to take.

An example of an area of the body where this poses a problem is the biliary tree, where wire guides are often introduced prior to procedures such as endoscopic retrograde cholangiopancreatography (ERCP), which is a diagnostic visualization technique commonly used with a sphincterotome. The biliary tree includes bifurcations at the junction of the biliary and pancreatic ducts and the right and left hepatic ducts. The anatomy of the biliary tree can make navigation of the wire guide into the desired branch of the bifurcation difficult.

In view of the difficulties of successfully navigating into and within a branched body passageway, there is a need for a medical device that can reliably gain access to and navigate through a branched body passageway.

SUMMARY

Accordingly, a medical sphincterotome for directing an elongate member into a selected body passageway is provided. According to a first aspect of the invention, the sphincterotome comprises a tubular member, a cutting wire, a wire guide lumen extending between a proximal portion and a distal port, and a deflection member disposed adjacent to the distal port. The tubular member has a proximal portion, a distal portion, and a longitudinal axis extending therebetween. The cutting wire has a conductor and a cutting edge. The conductor is disposed within a first longitudinal lumen and extends from the proximal portion to the cutting edge. The cutting edge is exposed along the distal portion. The cutting edge is oriented generally longitudinally relative to the longitudinal axis and extends radially outward relative to the longitudinal axis. The distal port is positioned proximal to a distal end of the tubular member. The wire guide lumen extends along the longitudinal axis from the proximal portion to the distal port. The deflection member is operably connected to the tubular member. The deflection member is disposed within the wire guide lumen and adjacent to the distal port. The deflection member is configured to direct the elongate member out through the distal port at an angle away from the longitudinal axis of the tubular member.

In a second aspect, a medical sphincterotome for directing an elongate member into a selected duct of a branched duct bodily lumen is provided. The sphincterotome comprises a tubular member and a cutting wire. The tubular member has a proximal portion, a distal portion, and a longitudinal axis extending therebetween. The distal portion of the tubular member comprises an offset nose-shaped end that has an end portion movable from a first position to a second position. The cutting wire has a conductor and a cutting edge. The conductor is disposed within a first longitudinal lumen, and the conductor extends from the proximal portion to the cutting edge. The cutting edge is exposed along the distal portion and is oriented generally longitudinally relative to the longitudinal axis and extends radially outward relative to the longitudinal axis. The offset nose-shaped end is adapted to move from the first position to the second position to substantially block a first duct of the branched duct bodily lumen. The blocking of the first duct forces the elongate member through a second longitudinal lumen and into the second duct.

In a third aspect, a method of using the sphincterotome to direct an elongate member is provided. The sphincterotome comprises a tubular member and a cutting wire. The tubular member has a proximal portion, a distal portion, and a longitudinal axis extending therebetween. The distal portion comprises an offset nose-shaped end that has an end portion that is configured to be movable from a first position to a second position. The cutting wire has a conductor and a cutting edge. The conductor is disposed within a first longitudinal lumen. The conductor extends from the proximal portion to the cutting edge. The cutting edge is exposed along the distal portion. The cutting edge is oriented generally longitudinally relative to the longitudinal axis and extends radially outward relative to the longitudinal axis of the tubular member. The sphincterotome is inserted into a branching body lumen having a first branch and a second branch adjacent to the first branch. The offset nose-shaped end of the sphincterotome is moved into the second position and is positioned into the first branch a predetermined amount that is sufficient for the offset nose-shaped end to block the entrance of the elongate member into the first branch. The elongate member is advanced through the second lumen out through the distal port in the offset nose-shaped end at an angle relative to the distal portion of the end, and into the second lumen.

In a fourth aspect, a method of using a sphincterotome to lift a papilla and gain access therethrough is provided. The sphincterotome comprises a tubular member, a cutting wire, and a deflection member. The tubular member has a proximal portion with a control handle located along it, a distal portion, and a longitudinal axis extending therebetween. The tubular member also has a distal portion and a longitudinal axis extending therebetween. The cutting wire has a conductor and a cutting edge. The conductor is disposed within a first longitudinal lumen. The conductor extends from the proximal portion to the cutting edge. The cutting edge is exposed along the distal portion and is oriented generally longitudinally relative to the longitudinal axis and generally radially outward relative to the longitudinal axis. The deflection member is disposed within a second longitudinal lumen. The deflection member is located along the distal portion of the tubular member and adjacent and distal to a distal port in the tubular member. The sphincterotome is positioned near the papilla. The cutting wire is oriented adjacent to the papilla. The control handle is then actuated to curl the distal portion of the tubular member to engage the papilla. The papilla is then lifted. After the papilla is lifted, a wire guide is advanced until contacting the deflection member. The deflection member is configured to deflect the wire guide through the distal port and away from the longitudinal axis.

BRIEF DESCRIPTION OF THE DRAWINGS

Embodiments will now be described by way of example with reference to the accompanying drawings, in which.

DETAILED DESCRIPTION OF THE PREFERRED EMBODIMENTS

Figure 1:
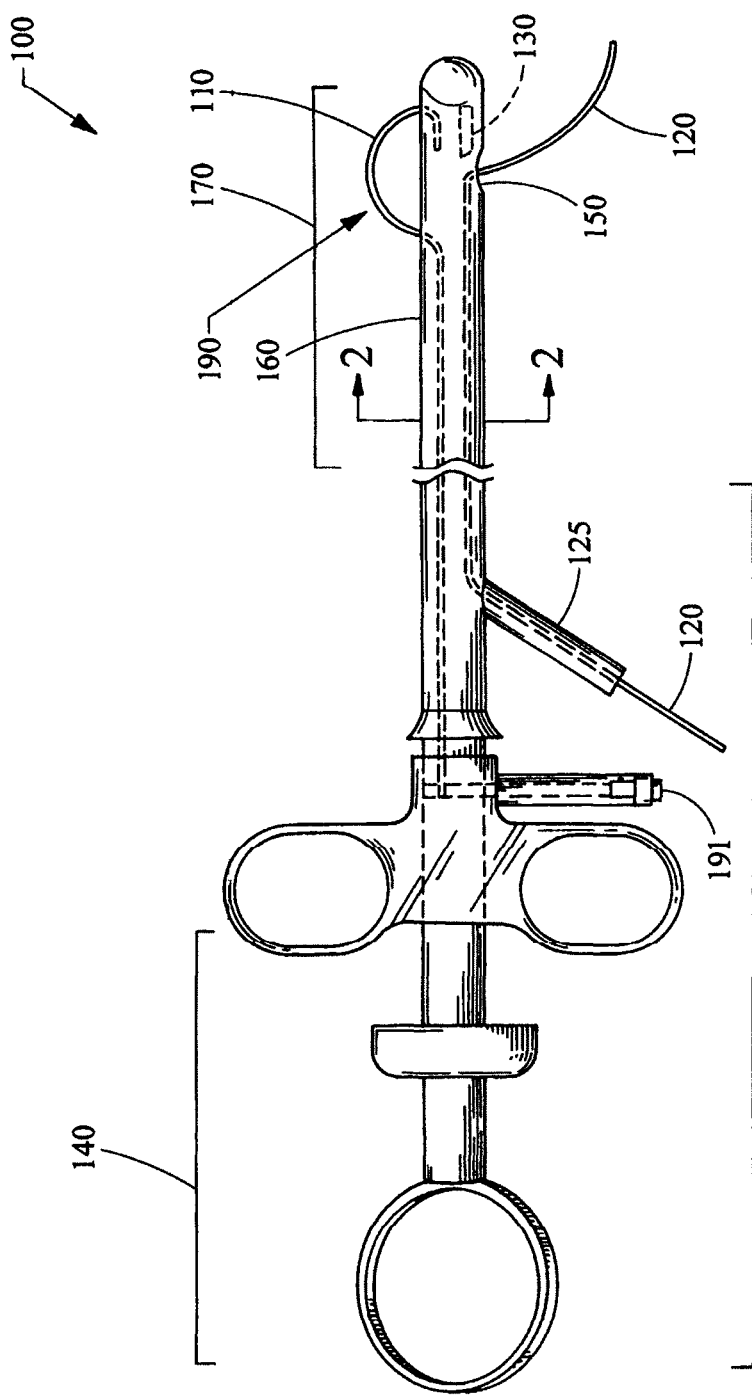
FIG. 1 is a side view of a sphincterotome in a relaxed state with a distal port and deflection member and loaded with a wire guide.

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted which are not necessary for an understanding of the embodiments, such as conventional details of fabrication and assembly.

An exemplary sphincterotome is shown in FIG. 1. FIG. 1 shows a sphincterotome 100 that is loaded with a wire guide 120. The sphincterotome 100 includes a tubular member 160 having a distal portion 170 and a proximal portion 180. The distal portion 170 of the tubular member 160 includes a cutting wire 190 with a cutting edge 110. The distal portion 170 of the tubular member 160 further includes a distal port 150 with an adjacent deflecting member 130. In general, the sphincterotome 100 enables the wire guide 120 to cannulate difficult to access body passageways, such as, by way of example, a branch of the biliary tree.

Tubular member 160 is preferably flexible and may be formed from any semi-rigid polymer such as polyurethane, polyethylene, tetrafluroethylene, polytetrafluoroethylene, fluorinated ethylene propylene, or the like. Tubular member 160 may also be formed from any metal or metallic alloy, including a shape memory alloy. Tubular member 160 may have a length ranging from about 190 centimeters to about 250 centimeters. In at least one embodiment, it is about 200 centimeters long. The tubular member 160 may have a diameter from at least about 5 French. Tubular member 160 may include multiple lumens. Preferably, there are at least two lumens as discussed further below. Other structural variations to the tubular member 160 are contemplated. For example, the tubular member 160 may take the form of a coiled spring for increased flexibility.

Figure 2:
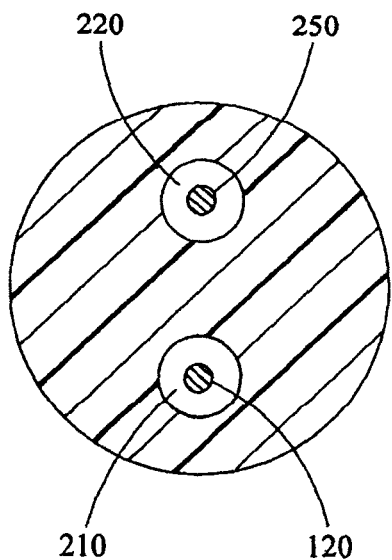
FIG. 2 is a cross-sectional view of FIG. 1 taken along line 2-2.
Figure 3:
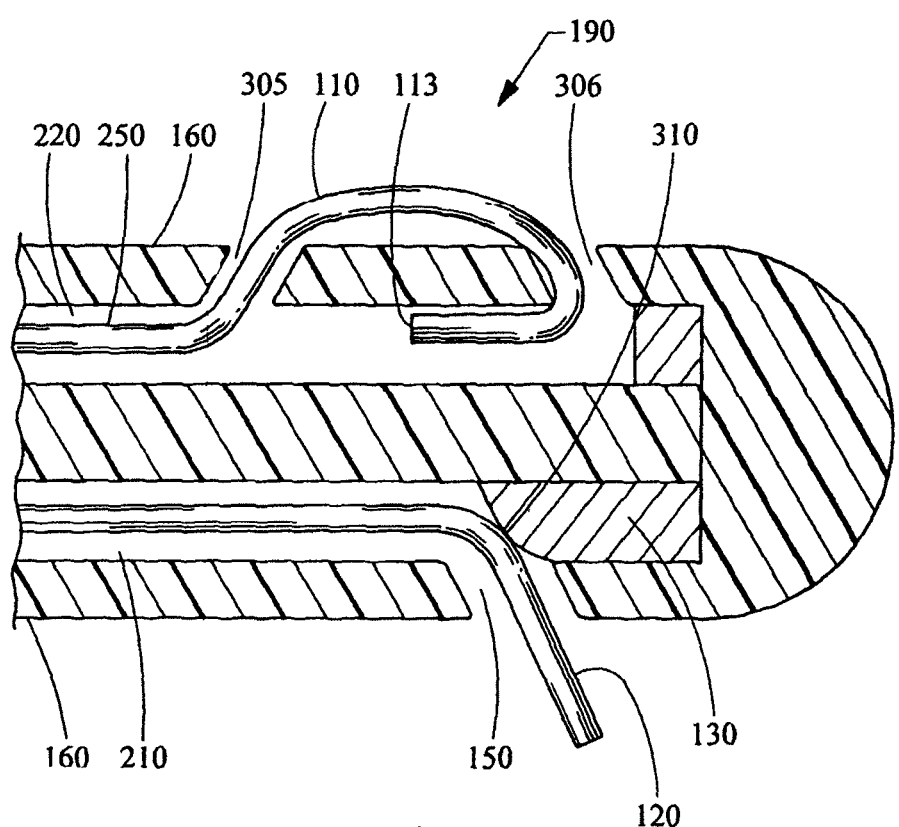
FIG. 3 is a cross-sectional view of FIG. 1 taken along the longitudinal axis.

FIG. 2 is a cross-sectional view taken along line 2-2 in FIG. 1. FIG. 2 shows a cutting wire lumen 220 and a wire guide lumen 210. The cutting wire lumen 220 contains the conductor 250 component of the cutting wire 190, as shown in FIG. 3. The wire guide lumen 210 contains the wire guide 120, which is fed through wire guide port 125, as shown in FIG. 1. The wire guide lumen 210 is generally oriented below the cutting wire lumen 220. As shown in FIG. 3, both the cutting wire lumen 220 and the wire guide lumen 210 terminate prior to reaching the distal end of the sphincterotome 100. Although lumens 210 and 220 are shown with circular cross-sectional shapes, other lumen shapes are possible. Although not shown in FIG. 2, the cutting wire lumen 220 may be larger than the wire guide lumen 210 to accommodate for the relatively larger conductor component 250 (FIG. 3) that may be disposed therewithin.

Referring to FIG. 3, the distal port 150 and deflection member 130 are configured to allow the wire guide 120 to be oriented away from the longitudinal axis of the tubular member 160 as it passes out through the distal port 150 so that it may enter the desired branched duct. The distal port 150 is placed proximal and adjacent to the deflection member 130. Deflection member 130 may be a metal or plastic insert or other material such as a cured adhesive material. The deflection member 130 is sufficiently rigid to deflect and direct the advancing wire guide 120 out of the wire guide lumen 210. The exact longitudinal placement of the distal port 150 and deflection member 130 along tubular member may be varied and is dependent on a variety of factors, including the location of the distal portion 170 of sphincterotome 100 within the branched anatomy, the orientation of the longitudinal axis of the sphincterotome 100 with respect to the desired branched duct, and the overall tortuosity of the branched vasculature. In the example shown, the distal end of the deflection member 130 is shown to longitudinally extend beyond the distal end of the cutting wire 190. The point of contact 310 at which the wire guide 120 first abuts the deflection member 130 is variable, depending on the shape and size of the deflection member 130. However, it is generally located at a point along the deflection member's 130 proximal or rearward portion such that the advancing wire guide 120 deflects from the deflection member 130 and is directed laterally and away from the longitudinal axis of the tubular member 160.

Still referring to FIG. 3, the cutting wire 190 contains a conductor component 250 and a cutting edge component 110. The cutting edge 110 is shown in FIGS. 1 and 3. The cutting edge 110 is located along the distal portion 170 of the tubular member 160. The cutting edge 110 is shown in its relaxed state to be oriented generally longitudinal with respect to the tubular member 160 and extending generally radially outward relative to the longitudinal axis of the tubular member 160. Actuation of the control handle assembly 140 moves the cutting edge 110 from its relaxed state into a predetermined cutting plane to cut tissue, such as a patient's sphincter muscle.

As shown in FIG. 3, conductor 250 is a wire running through cutting wire lumen 220 and is connected at its proximal end to connection 191 (FIG. 1) to provide a high frequency electrical current to conductor 250 and cutting edge 110 as is well known to one of ordinary skill in the art. Conductor 250 protrudes outward of the wall of tubular member 160 through first opening 305 to become cutting edge 110. The cutting edge 110 is bowed between the first opening 305 and the second opening 306 and is disposed outside of the wall of tubular member 160. The cutting edge 110 re-enters the wall of the tubular member 160 through second opening 306 and doubles back in a proximal direction through the cutting wire lumen 220 for several centimeters to its free end 113. Preferably, the conductor 250 and cutting edge 110 may be formed from a single wire, as shown in FIG. 3. Alternatively, the cutting edge and conductor may be distinct components that may be connected to each other by soldering or other conventional means.

The proximal end of the conductor component 250 is connected to the control handle assembly 140 such that actuation of the handle assembly 140 partially retracts (i.e., pulls in a proximal direction) the conductor component 250 relative to the tubular member 160. This actuation results in the distal portion 170 of tubular member 160 bowing to form an arc, with the exposed cutting wire 190 forming a secant of the arc.

Electric current passed through the conductor component 250 from electrical connection 191 in the control handle assembly 140 enables the cutting wire 190 to act as an electrosurgical cutting element that may be used effectively to cut and cauterize tissue, such as the sphincter of Oddi.

Figure 4:
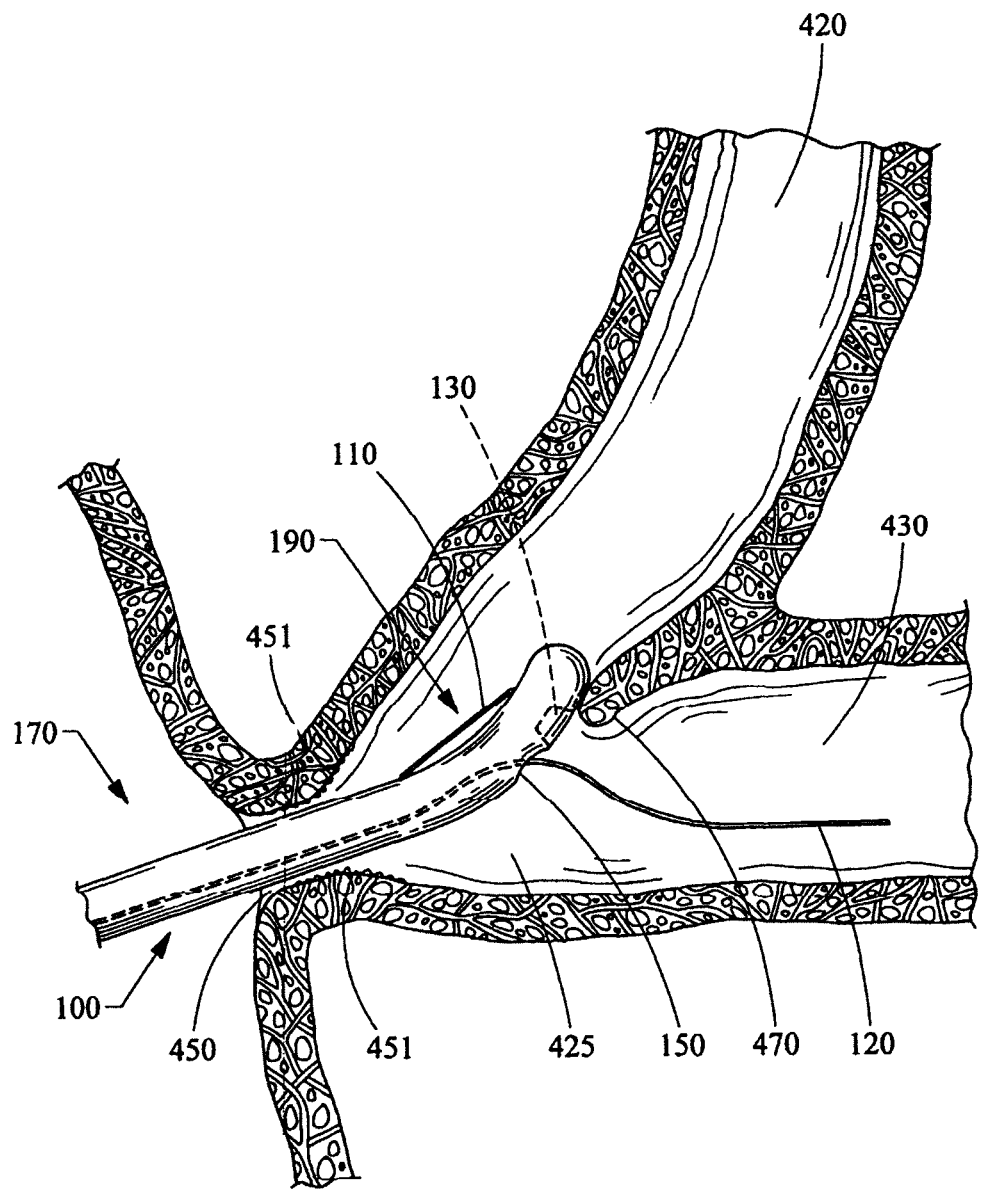
FIG. 4 is a method of using the sphincterotome of FIG. 1 in a biliary tree.
Figure 7:
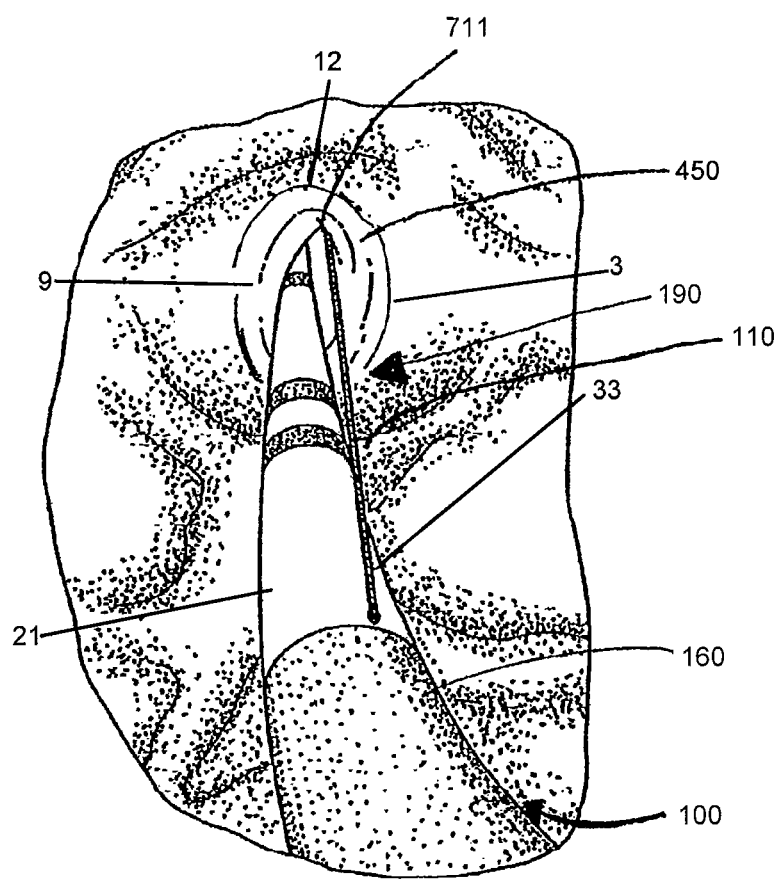
FIG. 7 is a perspective view of a sphincterotome accessing a patient's papilla.

A method for using sphincterotome 100 to direct a wire guide into a selected branched body passageway will now be described. In particular, FIG. 4 illustrates an exemplary procedure wherein the sphincterotome 100 may be used to direct a wire guide 120 into the pancreatic duct 430, which may be difficult to do with a standard sphincterotome because the sphincterotome and wire guide tend to follow a natural pathway into the biliary duct 420. The following procedure addresses this problem. An endoscope is advanced through the esophagus, gastrointestinal lumen, and into the duodenum until it is positioned in close proximity to the papilla 450. The sphincterotome 100 may then be loaded into an accessory channel of the endoscope. The sphincterotome 100 is generally in a straight configuration as it is loaded through the accessory channel. The sphincterotome 100 continues to be loaded through the accessory channel so that the distal portion 170 emerges from the distal end of accessory channel. The physician may use radiopaque markers that are selectively placed along the distal portion 170 to orient it such that the cutting wire 190 is configured into the 12 o'clock position relative to the papilla (FIG. 7). Referring to FIG. 7, the 12 o'clock position denotes that the cutting wire 190 of the sphincterotome 100 is oriented in the 12 o'clock position around the papilla 450. The 12, 3, and 9 designations, shown in FIG. 7, correspond to the positions of 12 o'clock, 3 o'clock, and 9 o'clock respectively around papilla 450. As known in the art, configuring the cutting wire 190 in a 12 o'clock position around the papilla 450 is the optimal position for cannulating the biliary tree. Such a configuration enables the cutting edge 110 to lift the roof 711 (FIG. 7) of the papilla 450 and then enter the biliary duct 420 without injuring the duodenal wall or the pancreatic duct 430. The physician may now activate control handle 140 to curl the distal portion 170 upwards an amount sufficient to lift the roof 711 (FIG. 7) of the papilla 450. As FIG. 7 shows, the cutting edge 110 is oriented generally longitudinally relative to the longitudinal axis of tubular member 160. The cutting edge 110 extends radially outward and, if needed, may engage the tissue of the papilla 450. The cutting wire 190 may be electrically energized as is known in the art to cut the papilla 450 and lift its folds 451 (FIG. 4). FIG. 4 shows the papilla 450 after the folds 451 have been lifted.

After access through the papilla 450 has been established, the sphincterotome 100 may be maneuvered into the Ampulla of Vater 425 (FIG. 4) which communicates with the bile duct 420 and the pancreatic duct 430. The distal portion 170 of the sphincterotome 100 is positioned within the Ampulla of Vater 425 such that the distal port 150 and the deflection member 130 are located proximal relative to the point of bifurcation 470. Although FIG. 4 shows the entire deflection member 130 located proximal to the point of bifurcation 470, the deflection member 130 may only have its proximal portion proximal to the point of bifurcation 470.

At this point, the physician may advance wire guide 120 distally through the wire guide lumen 210. The wire guide 120 will contact the deflection member 130. Upon contact, the wire guide 120 will deflect off of the deflection member 130, thereby causing the wire guide 120 to move away from the longitudinal axis of the sphincterotome 100 as it is directed out through distal port 150. As wire guide 120 emerges from the distal port 150, it will be directed into the desired pancreatic duct 430. During the advancement of wire guide 120, contrast media may be injected around the wire guide 120 through the wire guide lumen 210 to monitor the location of the radiopaque portions of the wire guide 120 relative to the target pancreatic duct 430. Alternatively, contrast media may be injected in a separate third lumen (not shown) of the sphincterotome 100.

After successful cannulation has been achieved, the sphincterotome 100 may be withdrawn from the Ampulla of Vater 425, leaving the wire guide 120 in place within the pancreatic duct 430 for subsequent medical procedures.

Performing the above described cannulation with sphincterotome 100 is advantageous compared to using a normal sphincterotome. Typically, when using a standard sphincterotome for cannulation, the wire guide exits at the distal tip of the sphincterotome. Exit of the wire guide at the distal tip may potentially cause the wire guide to catch on the numerous folds 451 (FIG. 4) inherent within the roof 711 of the papilla 450 (FIG. 7). Additionally, such a wire guide may become trapped at the sphincterotome tip, which is bowed upwards to lift the roof 711. Either scenario could potentially prevent access of the wire guide into the biliary or pancreatic duct. Accordingly, the sphincterotome 100 may enable the wire guide 120 to avoid contact with the numerous folds 451 (FIG. 4) of the papilla 710 and/or the curved distal end of the bowed sphincterotome 100.

As an alternative to withdrawing the sphincterotome 100 from the Ampulla of Vater 425 after successful cannulation, the sphincterotome 100 may be used in subsequent electrocutting procedures with the wire guide 120 remaining within the wire guide lumen 210. The wire guide 120 may help to provide reinforcement of the tubular member 160 of the sphincterotome 100 during electrocutting procedures. For example, the wire guide 120 may help to resist movement of the cutting edge 110 from a cutting plane when the sphincterotome 100 is electrocutting various tissue in the biliary 420 or pancreatic duct 430. The structural advantages of having the wire guide 120 loaded within the sphincterotome to maintain stability of the cutting plane are disclosed in U.S. Pat. No. 5,075,062 and are incorporated herein by reference. Furthermore, the reinforcement feature of the wire guide 120 may also provide rigidity to the lumens 210 and 220, thereby preventing them from collapsing.

Figure 5:
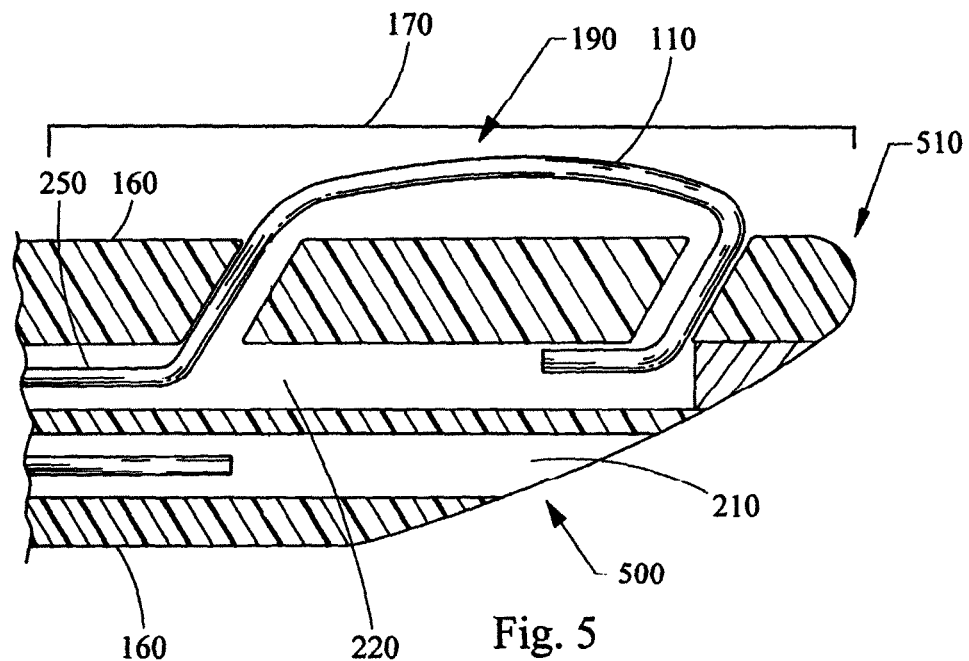
FIG. 5 is a longitudinal cross-sectional view of the distal portion of a sphincterotome with an offset nose-shaped distal end in a relaxed state.
Figure 6:
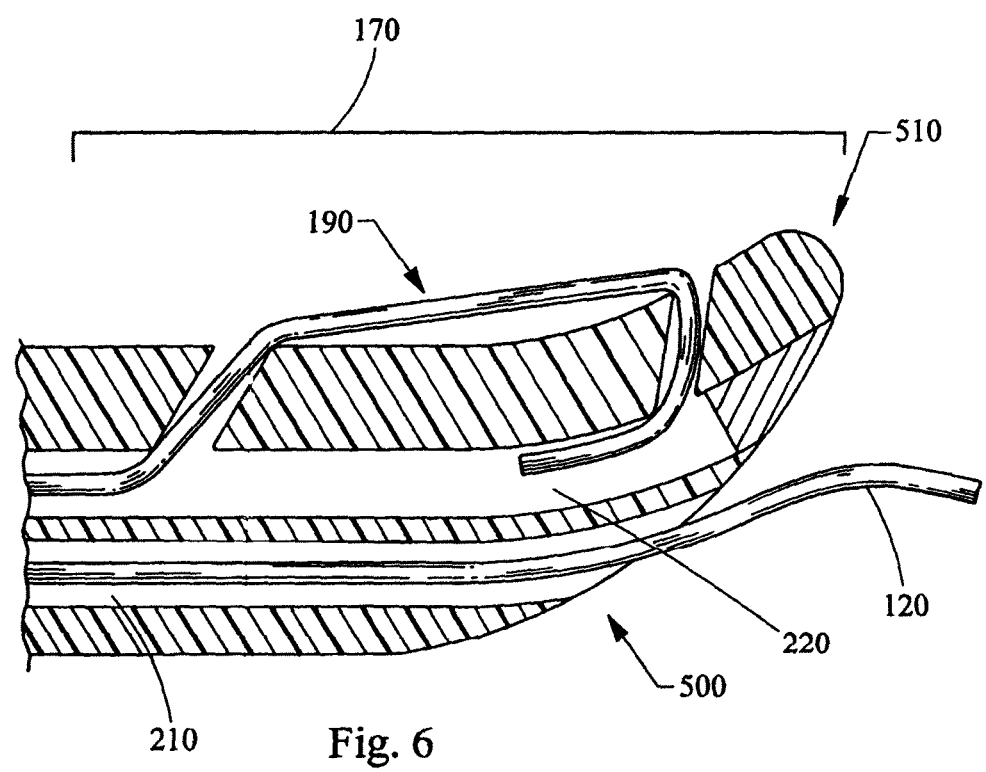
FIG. 6 is a longitudinal cross-sectional view of the sphincterotome of FIG. 5 with the offset nose-shaped end flexed and bent away from the longitudinal axis.

FIGS. 5 and 6 show another embodiment of the sphincterotome. In particular, the distal portion 170 of sphincterotome 500 is shown to have an offset nose-shaped end 510 at the distal end of the tubular member 160. The term "offset nose-shaped end" as used herein refers to a nose-shaped end 510 that is asymmetrical with respect to the longitudinal axis of the tubular member 160. Generally speaking, the offset nose-shaped end 510 is configured to bend when the cutting wire 190 is flexed such that the offset nose-shaped end 510 can block the wire guide 120 from entering an undesired branched body passageway. In the example provided above in which the wire guide 120 accesses the pancreatic duct 810 of a biliary tree, the offset nose-shaped end 510 would substantially block the biliary duct 420 such that the wire guide 120 would not be capable of inadvertently entering it. As a result, the distal port 150 and deflection member 130 of the first embodiment described above are not required to direct the wire guide 120 into the desired branched body passageway.

FIG. 5 shows the distal portion 170 of sphincterotome 500 with the offset nose-shaped end 510. The sphincterotome 500 is in an unflexed, relaxed state. The offset nose-shaped end 510 is asymmetrical with respect to the longitudinal axis of the tubular member 160. The end 510 is parallel to the longitudinal axis.

FIG. 6 shows the distal portion 170 of the sphincterotome 500 flexed to create a bowed configuration. An actuator such as a control handle 140 (FIG. 1) tensions the cutting wire 190, thereby bowing the offset nose-shaped end 510. In an exemplary procedure, the offset nose-shaped end 510 is bent and positioned to block the biliary duct 420, thereby forcing the wire guide 120 into the pancreatic duct 430 (FIG. 4). Depending on the particular anatomy of the branched body passageway to be blocked, it may only be necessary for the offset nose-shaped end 510 to be partially disposed within the passageway. Alternatively, in certain anatomies, the offset nose-shaped end 510 may remain outside of the branched body passageway and still be capable of preventing the wire guide 120 from entering the passageway. Although a nose-shaped end is shown, other geometries are contemplated that are capable of being bent to block a branched body passageway.

As an alternative to having an offset nose-shaped 510 end that bends upon flexing the cutting wire 190 (FIG. 6), the offset nose-shaped end 510 may be pre-curved to enable cutting of the papilla and blocking of the branched body passageway. The pre-curved tip may tend to resist movement of the cutting edge 110 of the cutting wire 190 out of the desired cutting plane thereby enabling the sphincterotome 500 to approach the papilla 450 (FIG. 4) at the desired angle for ease of cannulation and a consistent 12 o'clock orientation. The pre-curved nose-shaped distal end 510 of the sphincterotome 500 would allow the cutting wire 190 to automatically orient to the 12 o'clock position when the sphincterotome 500 emerges from the accessory channel 460 of the endoscope 470 (FIG. 4). After lifting the roof 711 (FIG. 7) of the papilla, the pre-curved offset nose-shaped 510 may be oriented to block one of the branched body passageways (e.g., the biliary duct) in order to allow the wire guide 120 to be navigated into the unblocked branched body passageway (e.g., the pancreatic duct). The extent of the pre-curvature of the offset nose-shaped end 510 may be varied to conform to the particular patient's anatomy.

An alternative sphincterotome may be a combination of the sphincterotome 100 of FIG. 1 and the sphincterotome 510 of FIG. 5 for potentially enhanced control of wire guide 120 navigation into a desired branched body passageway. In particular, the alternative sphincterotome may have a distal port 150 and deflection member 130 (FIG. 1) with an offset nose-shaped distal end 510 (FIG. 5). The sphincterotome may be used to selectively cannulate, by way of example, the pancreatic duct 430 of the biliary tree. The offset nose-shaped end 510 of the sphincterotome would be maneuvered partially into the biliary duct 420 a predetermined amount sufficient for the offset nose-shaped end 510 to block inadvertent entrance of the wire guide. Additionally, the distal portion 170 of the sphincterotome would be positioned such that the distal port 150 and at least a proximal portion of the deflection member 130 would be located proximal to the point of bifurcation 470 of the biliary tree. With this positioning, the wire guide 120 would be advanced through the wire guide lumen 210. The wire guide 120 would contact the deflection member 130, deflect off the deflection member 130, and exit through the distal port 150, and into the pancreatic duct 430 at an angle relative to the longitudinal axis of the tubular member 160. In this embodiment, the offset nose-shaped end 510 may provide a safeguard against inadvertent introduction of the wire guide 120 into the biliary duct 420.

The above described features of the sphincterotome are advantageous over conventional sphincterotomes because the sphincterotome as described in the above embodiments allow it to selectively cannulate within the biliary tree. In particular, unlike conventional sphincterotomes, the unique structural features of the above described sphincterotome allow it to selectively direct a wire guide in the biliary tree and navigate therewithin. Although the various embodiments of the sphincterotome have been discussed for use within the biliary tree, the unique design features of the sphincterotome allow it to be utilized in various other medical applications, including vascular applications.

The method of fabrication of the various embodiments of the sphincterotome will be apparent to one of ordinary skill in the art. Referring to FIG. 1, tubular member may be 160 extruded from the above-disclosed semi-rigid polymers by any of the conventional extruding techniques used in the catheter industry. Tubular member 160 may be formed with two or more lumens. Sphincterotome 500 with nose-shaped distal end 510 may also be extruded by conventional extruding techniques.

Conductor 250 may be threaded through the cutting wire lumen 220 from one end of the tubular member 160 to another. The conductor 250 may be threaded through the first opening 305 and then reenter the tubular wall through the second opening 306 (FIG. 3) to form the cutting wire 190 component. The free end of the conductor 250 that reenters the tubular wall through opening 306 may be threaded proximally back through the cutting wire lumen 220 (FIG. 3). If the conductor 250 and cutting wire 190 are formed from different wires, the proximal conductor component may be affixed to the proximal end of the cutting wire 190 at the first opening 305 (FIG. 3), and the distal conductor component may be a short anchor wire that is affixed to the distal end of the cutting wire 190 at the second opening 306 (FIG. 3). The affixing may be achieved through any means known to one of ordinary skill in the art, including soldering and welding.

The proximal end of the conductor 250 is attached to electrical connection 191 (FIG. 1) and control handle 140 as is known in the art. The proximal portion 180 of tubular member 160 is affixed to control 140 using adhesive or other means known in the art.

The distal port 150 may be formed by any conventional method, such as laser cutting, drilling, skiving, or mechanical punching. The deflection member 130 may be inserted into the wire guide lumen 210 manually by pushing the member through the lumen.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A medical sphincterotome device for directing an elongate member, comprising:
an elongate member;
a tubular member having a proximal portion, a distal portion, and a longitudinal axis extending therebetween;
a cutting wire comprising a conductor and a cutting edge, the conductor and the cutting edge each comprising a single wire, the conductor disposed within a cutting wire lumen extending along the longitudinal axis from the proximal portion to the distal portion of the tubular member, wherein the cutting wire lumen having a cutting wire lumen distal port disposed in a side wall of the distal portion of the tubular member, the conductor extending from the proximal portion to the cutting edge, the cutting edge being exposed along the distal portion, the cutting edge being oriented generally longitudinally relative to the longitudinal axis and extending radially outward relative to the longitudinal axis;

a wire guide lumen extending along the longitudinal axis from the proximal portion to the distal portion of the tubular member, the wire guide lumen having a distal port disposed in a side wall of the distal portion of the tubular member, the distal port being spaced proximally of a distal end of the tubular member, and the distal port positioned circumferentially offset and opposite from the cutting wire lumen distal port; and a non-movable deflection member operably connected to the tubular member, the non-movable deflection member disposed within the wire guide lumen and adjacent to the distal port, wherein the non-movable deflection member comprises a convex surface that is configured to engage and direct the elongate member out through the distal port at an angle away from the longitudinal axis of the tubular member, and wherein the wire guide lumen terminates at a rearward portion of the non-movable deflection member.

2. The device of claim 1, wherein the rearward portion of the non-movable deflection member is configured to engage a distal end of the elongate member.

3. The device of claim 1, wherein the elongate member is a wire guide.

4. The device of claim 1, wherein the sphincterotome is configured to selectively cannulate a bifurcated duct, the bifurcated duct comprising a first duct and a second duct.

5. The device of claim 4, wherein the first duct is a biliary duct and the second duct is a pancreatic duct.

6. The device of claim 1, wherein the distal portion is configured to be movable so as to lift a papilla, wherein lifting of the papilla achieves access of the elongate member therethrough.

7. The device of claim 6, wherein a control handle is operably connected to the distal portion, the control handle adapted to actuate movement of the distal portion.

8. The device of claim 1, further comprising a plurality of radiopaque markers affixed to the distal portion.

9. The device of claim 1, further comprising a plurality of lumens.

10. The device of claim 1, wherein the elongate member is configured to provide resistance against movement of the cutting edge from a cutting plane when the elongate member is disposed within the wire guide lumen.

11. A medical sphincterotome for directing an elongate member into a selected duct of a branched duct bodily lumen, comprising:

an elongate member;

a tubular member having a proximal portion, a distal portion, and a longitudinal axis extending therebetween, the distal portion terminating in an offset nose-shaped end having an asymmetric profile and comprising a sloped surface disposed along an acute angle relative to the longitudinal axis, the offset nose-shaped end being movable from a linear first configuration to a bent second configuration;

a wire guide lumen extending along the longitudinal axis from the proximal portion to the distal portion of the tubular member and terminating in a distal port disposed in the sloped surface of the offset nose-shaped end, the distal port being spaced proximally of a distal most portion of the offset nose-shaped end;

a cutting wire comprising a conductor and a cutting edge, the conductor and the cutting edge each comprising a single wire, the conductor disposed within a first longitudinal lumen extending along the longitudinal axis from the proximal portion to the distal portion of the tubular member, wherein the first longitudinal lumen having a cutting wire lumen distal port disposed in a side wall of the distal portion of the tubular member, the conductor extending from the proximal portion to the cutting edge, the cutting edge being exposed along the distal portion, the cutting edge being oriented generally longitudinally relative to the longitudinal axis and extending radially outward relative to the longitudinal axis, wherein the distal port positioned circumferentially offset and opposite from the cutting wire lumen distal port, wherein the cutting wire is operably connected to the offset nose-shaped end so as to move the offset nose-shaped end from a first position to a second position, the second position being configured to substantially block a first duct of the branched duct bodily lumen, the blocking of the first duct configured to direct the elongate member extending out through the distal port and into a second duct of the branched duct bodily lumen; and a deflection member disposed within the wire guide lumen and located along the distal portion of the tubular member, the deflection member being configured to engage and deflect the elongate member through the distal port at an angle relative to the longitudinal axis.

12. The sphincterotome of claim 11, wherein the first position is generally asymmetrical and parallel relative to the longitudinal axis.

13. The sphincterotome of claim 11, wherein the second position of the offset nose-shaped end is bent away from the longitudinal axis.

14. The sphincterotome of claim 11, wherein the tubular member is a coiled spring.

15. The sphincterotome of claim 11, wherein the offset nose-shaped end in combination with the deflection member of the sphincterotome is configured to selectively cannulate a branched body passageway.

16. The sphincterotome of claim 11, wherein the offset nose-shaped end is pre-curved a sufficient amount to enable selective cannulation of a branched body passageway.

* * * * *

UNITED STATES PATENT AND TRADEMARK OFFICE
CERTIFICATE OF CORRECTION

| | | |
|---|---|---|
| PATENT NO. | : 8,535,310 B2 | Page 1 of 1 |
| APPLICATION NO. | : 11/835837 | |
| DATED | : September 17, 2013 | |
| INVENTOR(S) | : Hardin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 62 days.

Signed and Sealed this
Twelfth Day of May, 2015

Michelle K. Lee
*Director of the United States Patent and Trademark Office*